United States Patent

Arena

[11] Patent Number: 4,717,696
[45] Date of Patent: Jan. 5, 1988

[54] REGENERATION OF A SUPPORTED PALLADIUM CATALYST USED IN THE CONVERSION OF CYANOHYDRINS TO THEIR ALDOSES

[75] Inventor: Blaise J. Arena, Des Plaines, Ill.
[73] Assignee: UOP Inc., Des Plaines, Ill.
[21] Appl. No.: 925,763
[22] Filed: Oct. 31, 1986
[51] Int. Cl.⁴ .................. B01J 29/36; B01J 38/62; B01J 38/60; C07H 1/00
[52] U.S. Cl. .................. 502/28; 127/30; 127/42; 502/27; 536/124
[58] Field of Search ............. 502/27, 28, 22; 127/30, 127/42; 536/1.1, 124

[56] References Cited

U.S. PATENT DOCUMENTS

| | | | |
|---|---|---|---|
| 2,704,281 | 3/1955 | Apell | 502/27 |
| 3,963,789 | 6/1976 | Kruse et al. | 568/863 |
| 4,207,413 | 6/1980 | Szarek et al. | 536/1 |
| 4,262,032 | 4/1981 | Levin | 426/658 |
| 4,371,616 | 2/1983 | Huibers | 435/105 |
| 4,421,568 | 12/1983 | Huibers | 127/40 |
| 4,439,414 | 3/1984 | Shive et al. | 127/30 |
| 4,440,855 | 4/1984 | Horwath et al. | 435/105 |
| 4,581,447 | 4/1986 | Arena | 536/124 |

OTHER PUBLICATIONS

M. L. Wolfrom, *J. Amer. Chem. Soc.*, 68, 791, 793 (1946).
E. Fischer, *Ber. Deutsch. Chem. Geo.*, 23, 370, 389 (1890).
The Handbook of sensory Physiology, vol. 4, pp. 241-245, *Nature*, 221, 555 (1969).
"The Theory of Sweetness", in Sweeterners & Sweetness, pp. 42-50.

Primary Examiner—Paul E. Konopka
Attorney, Agent, or Firm—Thomas K. McBride; John F. Spears, Jr.; Eugene I. Snyder

[57] ABSTRACT

Supported zerovalent palladium used in the hydrogenation of aldose cyanohydrins is rapidly deactivated. A regeneration procedure based on a water wash and acid treatment effectively restores catalyst activity to its original level. Such a regeneration procedure may be used over several cycles to afford a catalyst with essentially unaltered activity.

6 Claims, 1 Drawing Figure

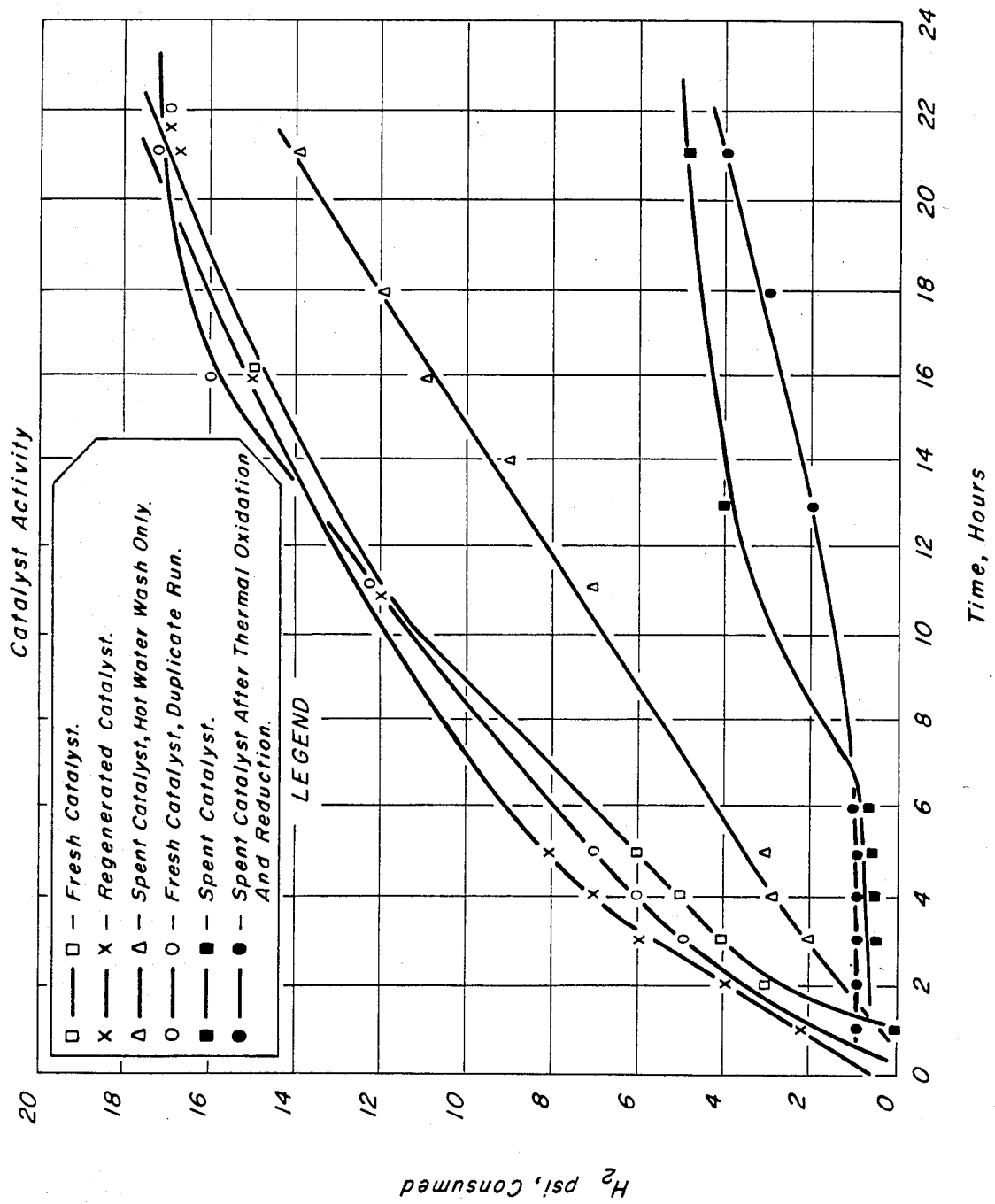

REGENERATION OF A SUPPORTED PALLADIUM CATALYST USED IN THE CONVERSION OF CYANOHYDRINS TO THEIR ALDOSES

BACKGROUND OF THE INVENTION

Present dietetic needs, predilections, and perceptions have led to the increased use of artificial sweeteners as a replacement for the "natural" sugars, including sucrose and fructose. Such artificial sweeteners are highly imperfect, including being under continual review for their long term physiological affects, yet their demand has grown unabated. Accompanying their growth as a commercial area with substantial economic impact has been a renewed emphasis on discovering and supplying new artificial sweeteners.

The ideal artifical sweetener would be noncaloric, noncariogenic, without detrimental physiological effects, and usable by diabetics. All these requirements would be met if a sweetener were not metabolized by humans and by flora which are found in the mouth and intestinal tract, and if the sweetener were either not absorbed by humans, or absorbed without effect on any internal organ. That is, the ideal sweetener should be excreted in the same form as when ingested. Another desirable feature is that it have bulk properties similar to sucrose so that it can be substituted for table sugar in many formulations. Recently, and perhaps belatedly, attention has turned toward the L-sugars as desirable artificial sweeteners. It has been known since at least 1946 that L-fructose is sweet (M. L. Wolfrom and A. Thompson, *J. Am. Chem. Soc.*, 68, 791, 793 (1946)), and since at least 1890 that L-fructose is nonfermentable (E. Fischer, *Ber. Deutsch. Chem. Ges.*, 23, 370, 389 (1890)), hence not metabolized by microorganisms generally metabolizing D-sugars. A reasonable, although not necessarily correct, inference is that it also is not metabolized by humans. Assuming that L-fructose is a sweet nonmetabolite it becomes obvious to use it as a noncaloric sweetener in many formulations. More recently Shallenberger and coworkers have demonstrated that many L-sugars have a sweetness comparable to their L-enantiomorphs. *Nature*, 221, 555 (1969). Cf. R. S. Shallenberger, "The Theory of Sweetness," in Sweeteners and Sweetness, pp 42–50, Edited by G. G. Birch and coworkers; R. S. Shallenberger and T. E. Acree in "The Handbook of Sensory Physiology," Vol. 4, pp 241–5, Edited by L. M. Beider (Springer Verlag, 1971).

Exploitation of the favorable properties of L-sugars is hindered by their relative unavailability. L-Fructose, for example, is not found to any significant extent in nature. This unavailability has spurred recent efforts in developing commercially feasible methods for preparing L-sugars in amounts necessary for their use as a staple of commerce. U.S. Pat. Nos. 4,371,616 and 4,421,568 describe a method of producing L-sugars, including L-idose and L-glucose, from the readily available D-glucose. Although the preparation of a number of L-sugars is described in U.S. Pat. No. 4,262,032 the focus seems to be on typical laboratory methods wholly unsuited or economical industrial production, in contrast to the process herein. U.S. Pat. No. 4,440,855 presents a flow scheme for the preparation of a mixture of L-glucose and L-mannose. The subject matter of U.S. Pat. No. 4,207,413 is L-sucrose, the enantiomer of ordinary table sugar, which can be hydrolyzed to afford L-fructose and L-glucose.

Many of the synthetic routes to L-sugars can be based on homologation in which a 1-carbon chain extension is effected by addition of the elements of HCN to an aldose. Conversion of the resulting cyanohydrin to an aldehyde group affords the next higher aldose, usually as an epimeric pair. One method of converting the cyanohydrin to an aldehyde is by catalytic hydrogenation with concomitant hydrolysis of the imine, the reduction product. The catalyst used must be active in effecting the reduction of a nitrile group to an imine, but must show little tendency to reduce either the imine initially formed or the aldehyde resulting from imine hydrolysis. Zerovalent palladium has been found to fill such requirements and often is used in cyanohydrin reduction. Supported palladium usually is preferred to colloidal palladium because of the ease of separation and recovery of the noble metal, as well as for increased catalyst activity. Because reduction of the cyanohydrin is performed under rather acidic conditions the support must be physically and chemically stable in acid solutions, a requirement which precludes the use of, for example, gamma-alumina, an otherwise popular support in catalytic reactions. The required acid resistance has necessitated the use of infrequently used and uncommon supports such as barium sulfate.

From the foregoing it is clear that hydrogenation of cyanohydrins with concomitant hydrolysis of the formed imine to an aldehyde is an uncommon process with uncommon catalyst requirements. To further complicate matters we have found that catalysts useful in the foregoing process are readily poisoned, being rendered effectively inactive after but one batch reduction, i.e., the catalysts cannot be reused. Of course this also implies that a continuous process employing such catalysts also is not feasible. Therefore it became mandatory to search for procedures which would regenerate catalyst activity.

The subject of this application is the regeneration of supported palladium catalysts for the reduction of cyanohydrins with concomitant hydrolysis to afford aldehydes as the final reaction product. More particularly it is directed toward catalyst regeneration when the catalyst is used in the reduction of cyanohydrins produced in homologation of sugars and when the product is an aldose.

SUMMARY OF THE INVENTION

The object of this invention is to regenerate supported palladium catalysts used in the reduction of cyanohydrins with concomitant hydrolysis to afford aldehydes (aldoses). An embodiment is treating used or spent catalyst first with hot water, then with an acid which is not oxidizing under treatment conditions at an elevated temperature. In a more specific embodiment the acid is hydrochloric acid. An acid wash temperature between about 40° and 100° C. represents another specific embodiment. Yet other embodiments will be apparent from the following.

DESCRIPTION OF THE FIGURE

The FIGURE shows the activity of various 5% palladium on barium sulfate catalysts used in the reduction of a mixture of gluco- and manno-cyanohydrins. Each curve is a plot of amount of hydrogen consumed versus time for a specific catalyst. The example should be consulted for additional details.

DESCRIPTION OF THE INVENTION

In the homologation of sugars the elements of HCN often are added to an aldose with formation of a cyanohydrin containing one carbon more than the original aldose. This cyanohydrin is then reduced with concomitant hydrolysis of the imine, which is the initial reaction product, to afford an aldehyde group. Thus the product is an aldose or an epimeric pair of aldoses having one carbon atom more than the reactant. The hydrogenation of the cyanohydrin usually is performed in an aqueous medium at a pH between about 1.0 and about 5.0 using as a catalyst zerovalent palladium supported on material which is stable under the reaction conditions. Our experience has been that the catalyst is rapidly deactivated, with little residual activity after its first use. Because of the expense associated with the catalyst preparation it became not merely desirable but rather necessary to develop a procedure which was itself simple, convenient to use, and very inexpensive by which catalytic activity could be regenerated.

The catalysts which are of interest in this application contain zerovalent palladium dispersed on an inert support. The supports which are used must be stable under hydrogenation conditions which include an aqueous reaction medium and a low pH, usually in the range between 1.0 and 5.0. Because of the unusual hydrogenation conditions the support used in the catalysts of interest here are relatively uncommonly used, and include materials such as barium sulfate, alpha-alumina, titania, titanated alumina, and carbon. Among these barium sulfate and alpha-alumina are most desirable supports for zerovalent palladium in the reduction of cyanohydrins.

The hydrogenation of cyanohydrins normally are batch reactions usually done under relatively low temperatures (often not over about 50° C.) and which occur over a period of about 12 hours. Normally the catalyst is largely deactivated within one batch reduction and is not useful thereafter. Such deactivation appears to arise from absorption of poisons which are present both before and arising during the hydrogenation, poisons which include some very highly colored material. We have discovered that the following procedure effectively regenerates the catalyst with recovery of virtually complete activity.

The initial step in the regeneration procedure is to thoroughly wash the catalyst with copious quantities of water. Initially much colored material is absorbed on the catalyst, material which contributes toward catalyst deactivation. The water wash removes most of these colored bodies, and the catalyst is washed with water until the wash is colorless. Generally this means that the deactivated catalyst is washed with from about 2 to about 10 volumes of water. The water wash can be performed at a temperature in the range from about 50° to about 100° C., but a wash temperature of from 80° to 100° C. appears most effective.

Following the water wash, the deactivated catalyst is then washed with acid. The acids which may be used at this stage are nonoxidizing acids under the wash conditions and also must be non-poisoning to palladium. Among the acids which can be used in the practice of this invention are included hydrochloric acid, sulfuric acid, nitric acid, trifluoroacetic acid, and acetic acid as representative of aliphatic carboxylic acids generally. The use of hydrochloric acid is recommended. Acids can be used in the concentration between about 1 and 4 molar, although acid concentration is not critical. The acid wash generally is conducted at a temperature between about 40° and about 100° C. with the range between 60° and about 90° C. being particularly desirable. The amount of acid used in the wash typically is from about 2 to about 10 volumes based on catalyst, although higher volumes can be used but without appreciably beneficial results. The contact time between the acid and catalyst will vary with temperature, acid concentration, volume of acid used, and history of the catalyst, but typical contact times are on the order of 2-6 hours.

After the catalyst is washed with acid it is then washed with a sufficient volume of water as to remove acid which has been absorbed by the catalyst. Typically water washing is continued until the wash has a pH greater than about 5. After washing is complete the catalyst is recovered and dried.

It has been observed that virtually complete recovery of catalyst activity may be had using the procedure described above. Additionally, the procedure can be used over several cycles so that the same catalyst can be used in several batch reactions with equivalent results. FIG. 1 shows results typical for initial and regenerated catalysts and shows the decrease in activity with reaction time for both the initial catalyst, once-used catalyst, and regenerated catalyst. These results point out rather strikingly that once-used catalyst is virtually inactive in a subsequent hydrogenation of a cyanohydrin, whereas the regenerated catalyst has essentially the same activity as fresh catalysts.

The example which follows is only illustrative of the invention as claimed and is not intended to be limiting in any way.

EXAMPLE

The catalyst used in a batch hydrogenation of a mixture of cyanohydrins resulting from the addition of HCN to L-arabinose was collected by filtration. This catalyst was washed with water at 90° C. until a clear supernatant was obtained. Washing was performed by mixing fresh portions of water with catalysts and decanting the supernatant. The solid was then washed in 4 liters of 3 molar hydrochloric acid at 80° C. for 4 hours. During this wash more colored material is desorbed from the catalyst. The hydrochloric acid solution was then decanted and the solid was washed repeatedly with deionized water until the supernatant had a pH of at least about 5 and was colorless. Excess water was removed by decantation and the catalyst slurry was dried at 80° C.

Cyanohydrin hydrogenations were performed as follows. To 25 mL of a freshly prepared solution of a mixture of gluco- and manno-cyanohydrin containing 15 weight percent cyanohydrins at pH 2.0 was added 2.1 g of 5% palladium on barium sulfate. This mixture was added to an 800 cc rotating glass-lined reactor, hydrogen was admitted, and reaction was effected at 60 psig hydrogen at 35° C. for 22 hours. Hydrogen consumption was measured periodically to afford the data upon which the various plots of FIG. 1 were obtained.

The FIGURE shows the activity of fresh catalyst (o—o and □—□) is reproducibly measurable, and that used catalyst regenerated as described above (x—x) is as active as fresh catalyst. However, spent catalyst (■—■), and spent catalyst first subjected to thermal oxidation (●—●) followed by reduction both showed very low activity, especially in the first 6 hours. Spent catalyst treated only with a hot water wash (Δ—Δ) exhibited intermediate activity.

What is claimed is:

1. In the process of reducing an aldocyanohydrin with concomitant hydrolysis to afford an aldose as the reduction product by hydrogenation of the aldocyanohydrin in an aqueous medium at a pH between about 1.0 and about 5.0 using as a catalyst zerovalent palladium dispersed on an inert support, the improvement whereby catalyst is regenerated by washing the deactivated catalyst with from about 2 to about 10 volumes of water at a temperature from about 50° to about 100° C., contacting the washed catalyst with from about 2 to about 10 volumes of a 1 to 4 molar solution of an acid at a temperature in the interval from about 40° to about 100° C. for a time from about 2 to about 6 hours, washing the acid-treated catalyst with water until the wash pH of the liquid after wash is at least 5, and recovering and drying the solid catalyst regenerated thereby.

2. The method of claim 1 where the aldocyanohydrin is the adduct of an aldose and hydrogen cyanide.

3. The method of claim 1 where the support is selected from the group consisting of barium sulfate, alpha-alumina, titania, titanated alumina, and carbon.

4. The method of claim 1 where the acid is selected from the group consisting of hydrochloric acid, sulfuric acid, nitric acid, trifluoroacetic acid, and acetic acid.

5. The method of claim 1 where the acid is hydrochloric acid.

6. The method of claim 5 where the temperature is between about 60° and 90° C.

* * * * *

UNITED STATES PATENT AND TRADEMARK OFFICE
CERTIFICATE OF CORRECTION

PATENT NO. : 4,717,696
DATED : January 5, 1988
INVENTOR(S) : Arena

It is certified that error appears in the above-identified patent and that said Letters Patent is hereby corrected as shown below:

In Column 5, line 6: Change "reduction" to --reaction--.

Signed and Sealed this

Twenty-fourth Day of May, 1988

Attest:

DONALD J. QUIGG

*Attesting Officer*   *Commissioner of Patents and Trademarks*